United States Patent
Herzog et al.

(10) Patent No.: US 6,696,596 B1
(45) Date of Patent: Feb. 24, 2004

(54) CATALYST AND METHOD FOR PRODUCING VINYL ACETATE

(75) Inventors: Bernhard Herzog, Oberursel (DE); Axel Schafer, Duisburg (DE); Karl H Renkel, Oberhausen (DE)

(73) Assignee: Celanese Chemicals Europe GmbH (DE)

( * ) Notice: Subject to any disclaimer, the term of this patent is extended or adjusted under 35 U.S.C. 154(b) by 0 days.

(21) Appl. No.: 10/031,264

(22) PCT Filed: Apr. 22, 2000

(86) PCT No.: PCT/EP00/03626

§ 371 (c)(1),
(2), (4) Date: Oct. 24, 2001

(87) PCT Pub. No.: WO00/66261

PCT Pub. Date: Nov. 9, 2000

(30) Foreign Application Priority Data

May 4, 1999  (DE) ......................... 199 20 390

(51) Int. Cl.$^7$ ................ C07C 67/05; C07C 67/02; B01J 23/58
(52) U.S. Cl. ................ 560/245; 560/243; 560/261; 502/330
(58) Field of Search ................ 560/243, 261, 560/245; 502/330

(56) References Cited

U.S. PATENT DOCUMENTS

| 3,637,819 A | 1/1972 | Sennewald et al. |
| 3,903,139 A | 9/1975 | Ferholz et al. |
| 6,376,706 B2 * | 4/2002 | Kitchen et al. |

FOREIGN PATENT DOCUMENTS

| EP | 0967009 | 12/1999 |

* cited by examiner

*Primary Examiner*—Porfirio Nazario-Gonzalez
*Assistant Examiner*—Paul A. Zucker
(74) *Attorney, Agent, or Firm*—Muserlian, Lucas and Mercanti

(57) ABSTRACT

A process for preparing vinyl acetate in the gas phase from ethylene, acetic acid and oxygen or oxygen-containing gases over a catalyst, consisting essentially of palladium and/or its compounds, gold and/or its compounds and alkali metal compounds on a support, wherein the catalyst further comprises vanadium and/or its compounds and catalyst therefrom.

8 Claims, No Drawings

CATALYST AND METHOD FOR PRODUCING VINYL ACETATE

This application is a 371 of PCT/EP00/03656 filed Apr. 22, 2000.

The present invention relates to a catalyst comprising palladium and/or its compounds, gold and/or its compounds, alkali metal compounds and vanadium and/or its compounds, and to its use for preparing vinyl acetate from acetic acid, ethylene and oxygen or oxygen-containing gases.

It is known that ethylene can be reacted in the gas phase with acetic acid and oxygen or oxygen-containing gases over fixed-bed catalysts comprising palladium/gold/alkali metal to give vinyl acetate.

The catalysts comprising palladium/gold/alkali metal generally have a particular noble metal distribution in which the noble metals are present in a shell on the support particles, while the core of the support particles is largely free of noble metals. The noble metal distribution in shell form is achieved by impregnation and subsequent precipitation of the noble metals using alkaline compounds. Catalysts having this noble metal distribution display a good activity and generally form little carbon dioxide and ethyl acetate. A further feature of these catalysts is that only small amounts of high boilers are formed when using these catalysts. Although these amounts are only small, they represent a problem in ecological and process engineering terms. Such high boilers are, for example, ethylidene diacetate, ethylene glycol and its acetates or diacetoxy ethylenes.

U.S. Pat. No. 3,775,342 discloses a process for producing catalysts comprising palladium, potassium and gold by impregnation of a support with a solution of palladium and gold salts, subsequent treatment with an alkaline solution which leads to water-insoluble palladium and gold compounds being deposited on the support and subsequent reduction of the metal compounds to the corresponding noble metals. Treatment of the support material with an alkali metal acetate solution can be carried out before or after the reduction step.

U.S. Pat. No. 4,048,096 teaches a process for producing catalysts comprising palladium, potassium and gold, in which process the support material is firstly impregnated with an aqueous solution containing a mixture of palladium and gold salts. Here, the volume of the impregnation solution corresponds to the pore volume of the support material. The moist support is subsequently completely covered with an aqueous alkaline solution, e.g. an aqueous sodium metasilicate solution, and left to stand at room temperature for 12 hours. In this way, the metal salts are converted into water-insoluble compounds and thus fixed to the support material. The palladium and gold compounds are reduced to the corresponding metals by subsequent treatment with a reducing agent. For this purpose, for example, an aqueous hydrazine solution is added with gentle agitation and the mixture is left to stand for 4 hours after the addition. After washing and drying, the support material laden with palladium and gold is treated with an alkali metal acetate solution and dried again. The catalyst obtained has a shell structure in which the palladium and gold are distributed over the surface of the support material in a shell thickness of about 0.5 millimeters.

In the process disclosed in U.S. Pat. No. 5,332,710 for producing a coated catalyst comprising palladium, gold and potassium, the support which has been impregnated with an aqueous palladium and gold salt solution is dipped into an aqueous fixing solution containing sodium hydroxide or potassium hydroxide and is agitated therein for at least 0.5 hour. In the fixing technique disclosed, the support which is completely covered by the fixing solution is agitated by rotation as from the commencement of the treatment with the fixing solution.

It has now surprisingly been found that the addition of vanadium and/or its compounds significantly improves the high-boiler selectivity of the catalyst. For the purposes of the present invention, the high boiler selectivity is the ratio of the amount of high boilers formed in the vinyl acetate synthesis to the amount of ethylene reacted. High boilers are, inter alia, the abovementioned compounds.

The invention accordingly provides a process for preparing vinyl acetate in the gas phase from ethylene, acetic acid and oxygen or oxygen-containing gases over a catalyst comprising palladium and/or its compounds, gold and/or its compounds and alkali metal compounds on a support, wherein the catalyst further comprises vanadium and/or its compounds.

The invention further provides a catalyst comprising palladium and/or its compounds, gold and/or its compounds and alkali metal compounds on a support, wherein the catalyst further comprises vanadium and/or its compounds.

The catalysts of the invention are preferably produced by:

(1) impregnating the support with a soluble vanadium compound and subsequently drying it;
(2) impregnating the pretreated support with soluble palladium and gold compounds;
(3) converting the soluble palladium and gold compounds on the support into insoluble compounds by means of an alkaline solution;
(4) reducing the insoluble palladium and gold compounds on the support by means of a reducing agent;
(5) washing the support and subsequently drying it;
(6) impregnating the support with a soluble alkali metal compound; and
(7) finally drying the support at not more than 150° C.

The steps (2) to (7) are known, for example, from U.S. Pat. Nos. 3,775,342; 4,048,096 and 5,332,710.

Apart from impregnation of the support with the soluble vanadium, palladium and gold compounds and also alkali metal compounds, it is also possible to employ other techniques known to those skilled in the art for applying the catalytically active substances to the support, for example multiple vapor deposition, spraying or dipping, if appropriate with use of ultrasound.

It is likewise possible to exchange steps (1) and (2), i.e. firstly to impregnate the support with a solution comprising palladium and gold compounds and, after drying, to apply a vanadium compound to the treated support.

Suitable supports are the known inert support materials such as silica, aluminum oxide, aluminosilicates, silicates, titanium oxide, zirconium oxide, titanates, silicon carbide and carbon. Particularly suitable supports of this type are those having a specific surface area of from 40 to 350 $m^2/g$ (measured by the BET method) and a mean pore radius of from 50 to 2000 Å (Ångström) (measured using mercury porosymmetry), especially silica ($SiO_2$) and $SiO_2$—$Al_2O_3$ mixtures. The supports used can have any shape, e.g. spheres, pellets, rings, stars or particles of other shapes, and their diameter or their length and thickness is generally in the range from 3 to 9 mm.

As support, it is possible to choose, for example, aerogenic $SiO_2$ or an aerogenic $SiO_2$—$Al_2O_3$ mixture which can be prepared, for example, by flame hydrolysis of silicon tetrachloride or a silicon tetrachloride/aluminum trichloride mixture in a hydrogen/oxygen flame (U.S. Pat. No. 3,939, 199).

The vanadium compound to be applied in step (1) is preferably a vanadium salt such as a vanadyl salt, a vanadate or an isopolyvanadate. Particular preference is given to using vanadyl salts such as chlorides, sulfates, oxalates, acetates and acetylacetonates. It is also possible to apply a plurality of vanadium salts and/or vanadyl salts, but just one vanadium salt or vanadyl salt is generally applied.

The elements palladium and gold to be applied in step (2) are preferably applied in the form of salt solutions, either individually in any order or together. Preference is given to using a single solution in which these elements to be applied are present in the form of salts. Particular preference is given to using a single solution in which just one salt of each of these elements to be applied is present.

In the case of interfering anions, e.g. chlorides, it has to be ensured that these anions are largely removed before the catalyst is used. This is achieved by washing the doped support, for example with water, after the palladium and gold applied, for example, as chloride have been converted into an insoluble form, for instance by fixing using alkaline compounds and/or by reduction (steps (3) and (4)).

Suitable salts of palladium and gold are all those which are soluble. Particularly suitable salts are chlorides, chloro complexes and carboxylates, preferably the salts of aliphatic monocarboxylic acids having from 2 to 5 carbon atoms, for example the acetate, propionate or butyrate. Further examples of suitable salts are the nitrate, nitrite, hydrated oxide, oxalate, acetylacetonate or acetoacetate. Owing to their good solubility and availability, the chlorides and chloro complexes of palladium and gold are particularly preferred as palladium and gold salts.

As alkali metal compound, preference is given to using at least one sodium, potassium, rubidium or cesium compound, in particular a potassium compound. Suitable compounds are especially carboxylates, in particular acetates and propionates. Other suitable compounds are ones which are converted into the alkali metal acetate under the reaction conditions, for instance the hydroxide, oxide or carbonate.

Suitable solvents for the palladium, gold, alkali metal and vanadium compounds are those in which the compounds chosen are soluble and which can easily be removed again by drying after the impregnation. If palladium, gold, alkali metal and vanadium salts are chosen, suitable solvents for the acetates and acetylacetonates are, in particular, unsubstituted carboxylic acids having from 2 to 10 carbon atoms, for example acetic acid, propionic acid, n- and iso-butyric acid and the various valeric acids. Owing to their physical properties and also for economic reasons, acetic acid is preferred among the carboxylic acids. For the chlorides, chloro complexes, acetato complexes and acetylacetonates, water is particularly suitable. The additional use of a further solvent is advantageous when the salts are not sufficiently soluble in acetic acid or in water. Thus, for example, palladium chloride dissolves significantly more readily in aqueous acetic acid than in glacial acetic acid. Possible additional solvents are those which are inert and are miscible with acetic acid or water. Suitable additives for acetic acid are ketones such as acetone and acetylacetone, also ethers such as tetrahydrofuran or dioxane, as well as hydrocarbons such as benzene.

If general reference is made in the following to "the solution of the salts", this applies analogously to the case where use is made of a succession of solutions which each contain only part of the total salts to be applied and in which the individual parts add up to the total amount of salts which are to be applied to the support.

In carrying out steps (1) and (2), the solution of the salts is applied to the support particles by impregnating them one or more times with this solution, where the total volume of solution can be used all at once or in two or more portions. However, it is advantageous to use the total volume of the salt solution all at once, so that the support particles are impregnated with the desired amount of the elements to be applied by a single impregnation step, which can be followed by immediate drying. In the case of successive impregnation with a plurality of portions of the solution, the particles are immediately dried after each impregnation.

Here, "immediate" drying means that drying of the impregnated particles has to be commenced promptly. In general, it is sufficient for drying of the particles to be commenced not more than ½ hour after the end of an impregnation step.

The impregnation of the support particles with the solution of the salts to be applied is carried out by covering the support particles with the solution and then pouring off or filtering off any excess solution. With a view to solution losses, it is advantageous to use only an amount of solution corresponding to the integrated pore volume of the catalyst support, so that the volume of the impregnation solution preferably corresponds to 98–100% of the pore volume of the catalyst support.

It is advantageous to mix the support particles intimately during impregnation, for example in a rotating or agitated flask or a mixing drum, which can be immediately followed by drying. The speed of rotation or intensity of agitation has to be sufficient to ensure good mixing and wetting of the support particles but must not be so great that significant abrasion of the support material occurs.

Treatment of the support particles impregnated in steps (1) and (2) with an alkaline solution converts the salts of the elements applied into water-insoluble compounds and thus fixes them to the support surface (step (3)).

As fixing solutions, it is possible to use, for example, aqueous alkaline solutions. Examples of such solutions are aqueous solutions of alkali metal silicates, alkali metal carbonates and hydrogencarbonates, alkali metal hydroxides or alkali metal borates.

Preference is given to an aqueous solution of alkali metal hydroxides, in particular potassium or sodium hydroxide. Aqueous solutions containing boron compounds can also be used as alkaline solutions. Here, aqueous solutions of borax (sodium tetraborate decahydrate), potassium tetraborate or mixtures of alkali metal hydroxide and boric acid are particularly suitable. The alkaline solution can have buffering properties.

The amount of alkaline compound present in the fixing solution is advantageously calculated so that it is at least sufficient for the stoichiometric conversion of the soluble palladium and gold compounds applied into water-insoluble compounds.

However, it is also possible to employ an excess of the alkaline compound present in the fixing solution; the excess is generally from 1 to 10 times the stoichiometrically required amount.

The volume of the fixing solution should be calculated so as to be at least sufficient to cover the impregnated support completely with the fixing solution. The fixing step is preferably carried out by the technique known from U.S. Pat. No. 5,332,710, which is hereby incorporated by reference. In this technique, the support which is completely covered with the fixing solution is agitated by rotation as from the commencement of the treatment with the fixing solution.

Any type of rotation or similar treatment which keeps the support particles in motion can be utilized, since the precise method is not critical. However, the intensity of the motion is important. This should be sufficient to wet the entire surface of the impregnated supports uniformly with the alkaline fixing solution.

The treated support is then left to stand in the fixing solution for up to 16 hours at room temperature in order to ensure that the palladium and gold compounds applied are completely precipitated in the form of water-insoluble compounds on the catalyst support.

The reaction on the support can be carried out at room temperature or else at elevated temperature, e.g. at 70° C.

The procedure for the subsequent reduction of the insoluble palladium and gold compounds (step 4) depends on whether a gaseous or liquid reducing agent is employed.

If a liquid reducing agent is employed, the liquid reducing agent is added after fixing is complete, if desired only after pouring off the supernatant fixing solution.

The reduction is carried out at a temperature of from 0° C. to 90° C., preferably from 15 to 25° C. Reducing agents which can be used are, for example, aqueous solutions of hydrazine, formic acid or alkali metal borohydrides, preferably sodium borohydride.

After the reduction, the treated catalyst support has to be washed a number of times (step (5)) to remove interfering compounds, e.g. to remove chloride residues which originate from the impregnation step and are liberated by the fixing and reduction of the noble metals.

For this washing step, the treated support is continuously washed at room temperature with the washing liquid, preferably using flowing, demineralized water, until interfering anions such as chlorides have been removed. The washing procedure also allows residues of the reducing agent used to be removed.

The moist catalyst precursor is subsequently dried at temperatures of not more than 150° C. (step 5).

If a gaseous reducing agent is employed, the supernatant fixing solution is firstly poured off after fixing is complete. Subsequently, it is advisable to wash the treated support obtained after the fixing step prior to the reduction step in order to remove the soluble compounds present on the treated support, e.g. the alkali metal chlorides liberated in the fixing step and any excess of the alkaline compound present in the fixing solution.

For this washing step, the treated support is continuously washed at room temperature with the washing liquid, preferably flowing, demineralized water. Washing is continued until interfering anions, e.g. chlorides, have been largely removed from the support. Subsequently, it is advantageous to dry the moist impregnated catalyst support prior to the reduction carried out using a gaseous reducing agent. Drying is carried out at temperatures of not more than 150° C.

The subsequent reduction is carried out at a temperature of generally from 40 to 260° C., preferably from 70 to 200° C. It is generally advantageous to use a reducing agent diluted with inert gas and containing from 0.01 to 50% by volume, preferably from 0.5 to 20% by volume, of reducing agent for the reduction. Examples of inert gases which can be used are nitrogen, carbon dioxide or a noble gas. Suitable reducing agents are, for example, hydrogen, methanol, formaldehyde, ethylene, propylene, isobutylene, butylene or other olefins.

Regardless of whether the reduction is carried out in the presence of a gaseous reducing agent or using a liquid reducing agent, the amount of reducing agent should be calculated on the basis of the amount of noble metals; the reduction equivalent should be at least equal to the oxidation equivalent, although larger amounts of reducing agent do no harm.

In the reduction step, it is essential to choose reaction conditions under which the fixed water-insoluble noble metal compounds are reduced to the corresponding noble metals. On the other hand, it is unimportant whether the vanadium present in vanadium compounds is also converted into elemental vanadium under the chosen reduction conditions, since this is not critical to the suitability of the catalysts of the invention for preparation of vinyl acetate.

The catalyst precursor obtained after the reduction step and possibly the drying step is, in step (6), treated, preferably impregnated, one or more times with a solution of an alkali metal compound, with the total volume of the solution being used all at once or in portions. However, it is advantageous to use the total volume of the solution all at once, so that the support particles are impregnated with the desired amounts of alkali metal compound to be applied by means of a single impregnation step. The solution volume of the alkali metal compound is, in both single and multiple impregnation, generally from 60 to 110%, preferably from 80 to 100%, of the pore volume.

The solution of the alkali metal compound can also be applied to the catalyst precursor by single or multiple spraying, vapor deposition or dipping.

After treatment with a solution of an alkali metal compound, the catalyst precursor is finally dried at not more than 150° C. (step (7)).

The alkali metal compound is used in such an amount that the finished catalyst after drying contains from 0.1 to 10% by weight of alkali metal.

The drying steps for the treated catalyst supports or the catalyst precursors are carried out in a hot air stream or in an inert gas stream, for example in a stream of nitrogen or carbon dioxide. The temperature during drying should generally be in the range from 60 to 150° C., preferably from 100 to 150° C. If desired, drying is carried out under reduced pressure, in general at from 0.01 MPa to 0.08 MPa.

The finished coated catalysts comprising palladium, gold, alkali metal and vanadium have the following metal contents:

| | |
|---|---|
| palladium content: | generally 0.5–2.0% by weight, preferably 0.6–1.5% by weight; |
| gold content: | generally 0.2–1.3% by weight, preferably 0.3–1.1% by weight; |
| alkali metal content: | generally 0.3–10% by weight, |
| preference is given to using potassium, | |
| potassium content: | generally 0.5–4.0% by weight, preferably 1.5–3.0% by weight; |
| vanadium content: | generally 0.01–1% by weight, preferably 0.05–0.5% by weight. |

The percentages indicated in all cases apply to the amounts of the elements palladium, gold, alkali metal and vanadium present in the finished catalyst, based on the total mass of the catalyst (active elements plus anions plus support material).

In the catalysts of the invention, the noble metals are present in the form of a shell on the support particles.

The preparation of vinyl acetate is generally carried out by passing acetic acid, ethylene and oxygen-containing gases over the finished catalyst at temperatures of from 100 to 220° C., preferably from 120 to 200° C., and pressures of from 0.1 to 2.5 MPa, preferably from 0.1 to 2.0 MPa, with unreacted components being able to be circulated. Dilution with inert gases such as nitrogen or carbon dioxide is sometimes also advantageous. Carbon dioxide is particularly suitable for dilution, since it is formed in small amounts during the reaction.

The activity and selectivity can be improved by means of the catalysts of the invention, as a result of which, in particular, high boiler formation is significantly reduced. High boilers are, in particular, the compounds mentioned at the outset which represent a problem in both ecological and process engineering terms.

The vinyl acetate process carried out using the catalysts of the invention thus also gives a higher yield of vinyl acetate, which makes the work-up of the crude vinyl acetate obtained easier, since the vinyl acetate content in the gas leaving the reactor is higher, which in turn leads to an energy saving in the work-up section. A suitable work-up is described, for example, in U.S. Pat. No. 5,066,365.

The following examples illustrate the invention but do not restrict it. The percentages of the elements palladium, gold, potassium and vanadium are percentages by weight based on the total mass of the finished catalyst.

EXAMPLES

In all examples, 7 mm pellets of KA-160 silica based on bentonite from Süd-Chemie served as support material.

Example 1

0.17 g (0.0007 mol) of vanadyl acetylacetonate were dissolved in 32 ml of demineralized water and applied to 52.4 g of support material. The treated support was then dried at 100° C. for 2 hours.

2.15 g (0.0066 mol) of $K_2PdCl_4$ and 0.77 g (0.002 mol) of $KAuCl_4$ were together weighed into a container and dissolved in 32 ml of demineralized water. All of the solution was applied to the pretreated support with gentle agitation. Subsequently, the material was dried at 100° C. for 2 hours.

To form a noble metal shell and convert the noble metal salts into insoluble compounds, a solution of 1.74 g (0.031 mol) of potassium hydroxide in 32 ml of demineralized water was poured over the pretreated support. To complete the reaction, the reaction mixture was allowed to stand for 14 hours and then washed free of chloride using demineralized water. The absence of chloride was tested by means of $AgNO_3$ detection of chloride ions in aqueous solution. The material was subsequently dried at 100° C. for 2 hours.

The noble metals were subsequently reduced by means of diluted ethylene (5% by volume in nitrogen). For this purpose, the gas mixture was passed over the catalyst at 150° C. for 5 hours. Subsequently, 4 g (0.041 mol) of potassium acetate were dissolved in 32 ml of demineralized water and added to the catalyst precursor a little at a time and the latter was dried again at 100° C. for 2 hours.

The finished catalyst contained 1.21% by weight of palladium, 0.69% by weight of gold, 2.75% by weight of potassium and 0.06% by weight of vanadium.

Example 2

0.42 g (0.0016 mol) of vanadyl acetylacetonate were dissolved in 40 ml of demineralized water and applied to 65.5 g of support material. The treated support was then dried at 100° C. for 2 hours.

2.69 g (0.0082 mol) of $K_2PdCl_4$ and 0.96 g (0.0025 mol) of $KAuCl_4$ were together weighed into a container and dissolved in 40 ml of demineralized water. All of the solution was applied to the pretreated support with gentle agitation. To form a noble metal shell and convert the noble metal salts into insoluble compounds, the pretreated support was introduced into a solution of 1.91 g (0.034 mol) of potassium hydroxide in 150 ml of demineralized water and the total reaction mixture was agitated on a rotary evaporator at a rotation rate of 5 rpm for 2.5 hours for the reaction to proceed to completion. To complete the reaction, the reaction mixture was allowed to stand for 14 hours and then washed free of chloride using demineralized water. The absence of chloride was tested by means of $AgNO_3$ detection of chloride ions in aqueous solution. The material was subsequently dried at 100° C. for 2 hours.

The noble metals were subsequently reduced by means of diluted ethylene (5% by volume in nitrogen). For this purpose, the gas mixture was passed over the catalyst at 150° C. for 5 hours. Subsequently, 5 g (0.051 mol) of potassium acetate were dissolved in 32 ml of demineralized water and added to the catalyst precursor a little at a time and the latter was dried again at 100° C. for 2 hours.

The finished catalyst contained 1.21% by weight of palladium, 0.69% by weight of gold, 2.75% by weight of potassium and 0.11% by weight of vanadium.

Comparative Example 1

5.37 g (0.0164 mol) of $K_2PdCl_4$ and 1.92 g (0.005 mol) of $KAuCl_4$ were together weighed into a container and dissolved in 80 ml of demineralized water. All of the solution was applied to 131 g of the support material with gentle agitation. Subsequently, the material was dried at 100° C. for 2 hours.

To form a noble metal shell and convert the noble metal salts into insoluble compounds, a solution of 3.81 g (0.068 mol) of potassium hydroxide in 80 ml of demineralized water was poured over the pretreated support. To complete the reaction, the reaction mixture was allowed to stand for 14 hours and then washed free of chloride using demineralized water. The absence of chloride was tested by means of $AgNO_3$ detection of chloride ions in aqueous solution. The material was subsequently dried at 100° C. for 2 hours.

The noble metals were subsequently reduced by means of diluted ethylene (5% by volume in nitrogen). For this purpose, the gas mixture was passed over the catalyst at 150° C. for 5 hours. Subsequently, 10 g (0.102 mol) of potassium acetate were dissolved in 77 ml of demineralized water and added to the catalyst a little at a time and the latter was dried again at 100° C. for 2 hours.

The finished catalyst contained 1.21% by weight of palladium, 0.69% by weight of gold and 2.75% by weight of potassium.

Comparative Example 2

2.69 g (0.0082 mol) of $K_2PdCl_4$ and 0.96 g (0.0025 mol) of $KAuCl_4$ were together weighed into a container and dissolved in 40 ml of demineralized water. All of the solution was applied to 65.5 g of the support material with gentle agitation. To form a noble metal shell and convert the noble metal salts into insoluble compounds, the pretreated support was introduced into a solution of 1.91 g (0.034 mol) of potassium hydroxide in 150 ml of demineralized water and the total reaction mixture was agitated on a rotary evaporator at a rotation rate of 5 rpm for 2.5 hours for the reaction to proceed to completion. To complete the reaction, the reaction mixture was allowed to stand for 14 hours and then washed free of chloride using demineralized water. The absence of chloride was tested by means of $AgNO_3$ detection of chloride ions in aqueous solution. The material was subsequently dried at 100° C. for 2 hours.

The noble metals were subsequently reduced by means of diluted ethylene (5% by volume in nitrogen). For this purpose, the gas mixture was passed over the catalyst at 150° C. for 5 hours. Subsequently, 4 g (0.041 mol) of potassium acetate were dissolved in 32 ml of demineralized water and added to the catalyst a little at a time and the latter was dried again at 100° C. for 2 hours.

The finished catalyst contained 1.21% by weight of palladium, 0.69% by weight of gold and 2.75% by weight of potassium.

To examine the performance of the catalysts described in the preparation of vinyl acetate, tests were carried out in a Berty reactor using a feed composition of 8.0% by volume of oxygen, 37.5% by volume of ethylene, 15.7% by volume of acetic acid and 38.8% by volume of nitrogen. The results are summarized in Table 1:

TABLE 1

| | Catalyst tests | |
| --- | --- | --- |
| Example | Space-time yield | High boiler selectivity |
| 1 | 683 | 0.5 |
| Comparative Example 1 | 688 | 1.1 |
| 2 | 732 | 0.8 |
| Comparative Example 2 | 698 | 1.5 |

Space-time yield in g of vinyl acetate/l of catalyst.h;
High boiler selectivity in mol %, based-on the amount of ethylene reacted.

As the data in the above table demonstrate, even small additions of vanadium to the known catalysts comprising palladium, gold and potassium lead to a significant reduction in high boiler formation in the preparation of vinyl acetate while simultaneously increasing the performance (space-time yield) of the catalysts of the invention.

What is claimed is:

1. A process for preparing vinyl acetate in the gas phase from ethylene, acetic acid and oxygen or oxygen-containing gases over a catalyst, consisting essentially of palladium and/or its compounds, gold and/or its compounds and alkali metal compounds on a support, wherein the catalyst further comprises vanadium and/or its compounds.

2. The process as claimed in claim 1, wherein the catalyst comprises at least one potassium compound.

3. The process as claimed in claim 1, wherein the catalyst contains 0.01% by weight to 1% by weight of vanadium, based on the total mass of the catalyst.

4. The process of claim 1, wherein the catalyst contains 0.05% by weight to 0.5% by weight of vanadium, based on the total mass of the catalyst.

5. A catalyst consisting essentially of palladium and/or its compounds, gold and and/or its compounds and alkali metal compounds on a support, wherein the catalyst further comprises vanadium and/or its compounds.

6. A catalyst as claimed in claim 5 which comprises at least one potassium compound.

7. A catalyst of claim 5 which contains 0.1% by weight to 1% by weight of vanadium, based on the total mass of the catalyst.

8. A catalyst of claim 5 which contains 0.05% by weight to 0.5% by weight of vanadium, based on the total mass of the catalyst.

* * * * *

UNITED STATES PATENT AND TRADEMARK OFFICE
CERTIFICATE OF CORRECTION

PATENT NO. : 6,696,596 B1
DATED : February 24, 2004
INVENTOR(S) : Bernhard Herzog et al.

It is certified that error appears in the above-identified patent and that said Letters Patent is hereby corrected as shown below:

<u>Title page,</u>
Item [75], Inventors, add -- Tao Wang, Corpus Christi (TX) --.

Signed and Sealed this

Fourth Day of April, 2006

JON W. DUDAS
*Director of the United States Patent and Trademark Office*